United States Patent [19]

Oliver et al.

[11] 4,181,282
[45] Jan. 1, 1980

[54] CASSETTE HOLDER

[76] Inventors: George D. Oliver, 29 Overlook Cir., Elizabethtown, Pa. 17022; Joseph T. Eisenhoffer, 5418 Devonshire, St. Louis, Mo. 63109; Joseph H. Eisenhoffer, 5320 Daggett, St. Louis, Mo. 63110

[21] Appl. No.: 809,024

[22] Filed: Jun. 22, 1977

[51] Int. Cl.² .................................... A47B 97/04
[52] U.S. Cl. .................................. 248/448; 248/451; 248/455; 248/460
[58] Field of Search ............... 248/448, 451, 452, 453, 248/454, 455, 456, 457, 460, 465

[56] References Cited

U.S. PATENT DOCUMENTS

| 401,662 | 4/1889 | Snow | 248/451 |
|---|---|---|---|
| 456,089 | 7/1891 | Harrison | 248/452 |
| 1,846,988 | 2/1932 | Buck | 248/460 X |
| 1,869,278 | 7/1932 | Ramelli | 248/455 |
| 2,003,746 | 6/1935 | Headington | 248/452 |
| 2,219,091 | 10/1940 | Henderson | 248/452 |
| 3,408,032 | 10/1968 | Francis | 248/451 X |
| 3,715,097 | 2/1973 | Kalajian | 248/460 X |
| 4,116,413 | 9/1978 | Andersen | 248/451 |

Primary Examiner—William H. Schultz
Attorney, Agent, or Firm—Cohn, Powell & Hind

[57] ABSTRACT

This cassette holder is for use with a medical examination table and an X-ray camera and includes a generally horizontal base plate having a holder plate hingedly attached thereto for swinging movement of the holder plate into a selected angle of inclination relative to the base plate to suit the position of the camera. A support linkage, hingedly attached to the base plate, clamps the holder plate in the selected position and the holder plate includes adjustably spaced cassette retaining arms. A modified cassette holder includes a slotted base plate which cooperates with a tracked table to provide longitudinal and transverse adjustment relative to the table.

6 Claims, 9 Drawing Figures

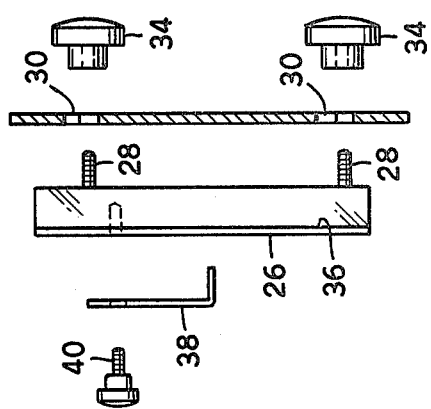
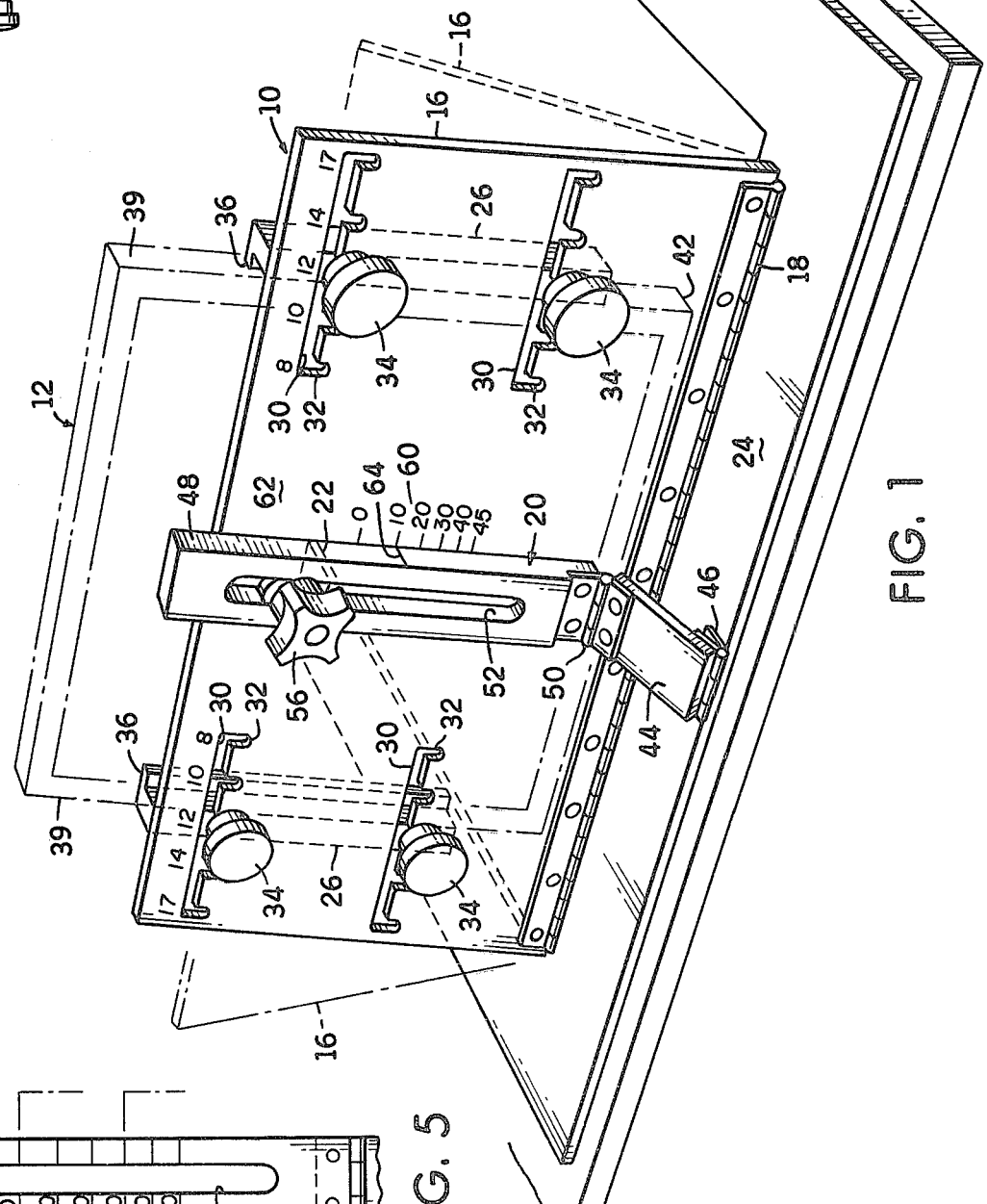
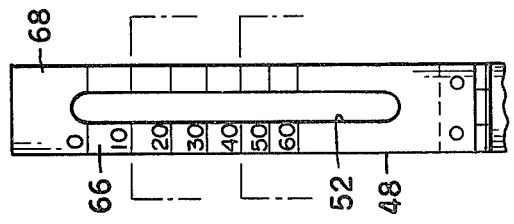

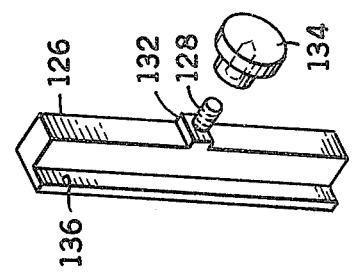
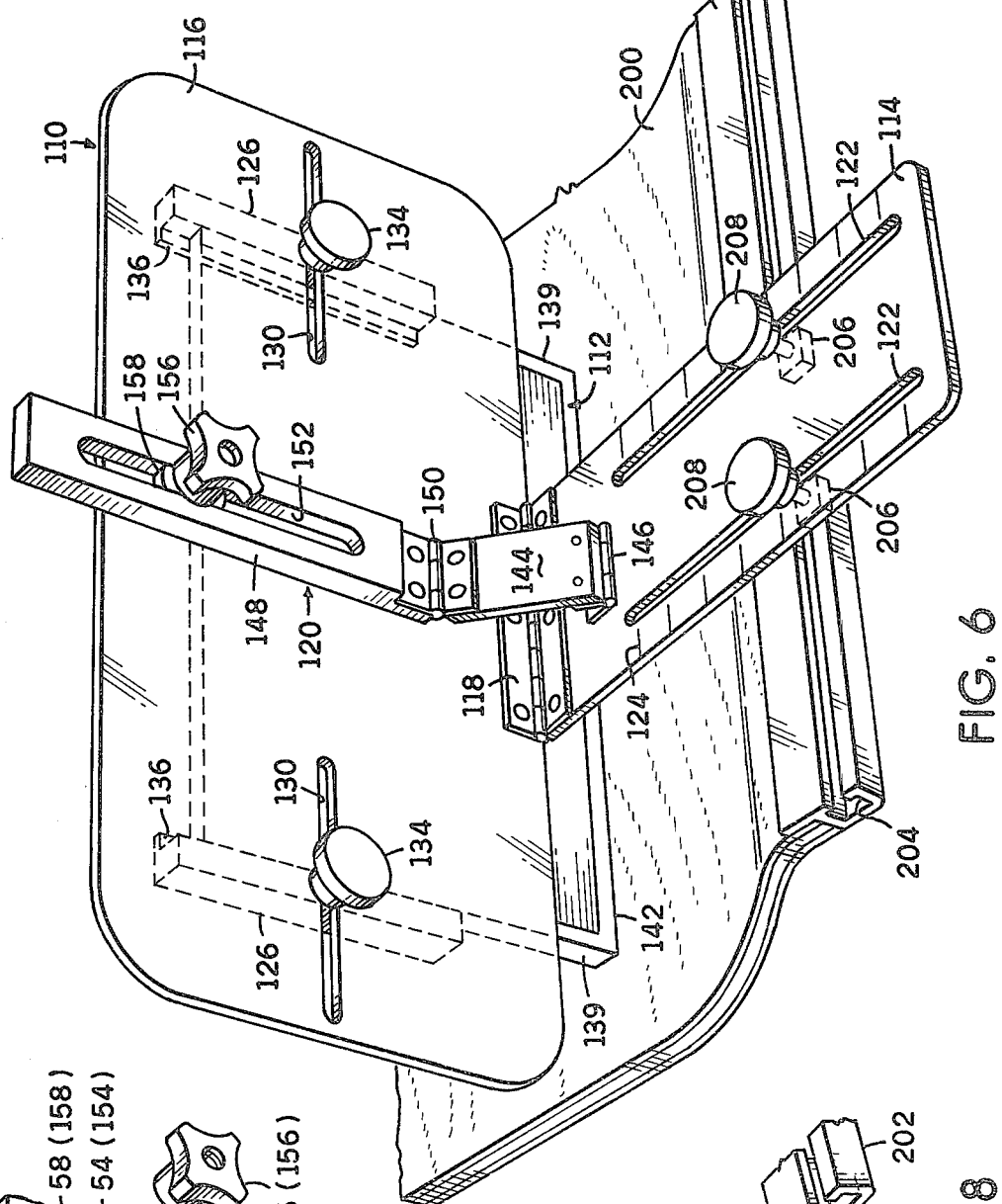
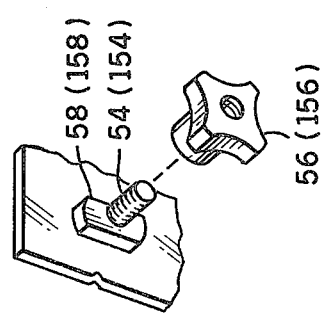
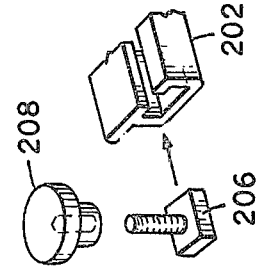

CASSETTE HOLDER

BACKGROUND OF THE INVENTION

This invention relates generally to holders and particularly to a holder for an X-ray cassette.

In conventional X-ray medical technology it is customary to use X-ray film mounted in cassettes. These cassettes are generally rectangular in configuration and include a peripheral frame which is held in the required position while taking the X-ray picture. It is desirable in many instances to hold the X-ray film at a particular angle and equally desirable that this angle should be adjustable. The provision of this feature on a simple table mounted base, having a hinged flap held in place by a conventional slotted arm such as is used for cabinets, presents a serious problem in that the angle adjusting mechanism lies at least in part in the area between the film and the patient.

An alternative type of holder in the known prior art consists of a box-like mobile unit mounted on a pedestal and having a top portion which opens and is held in position by means of a pair of clampable inclined side arms. This particular unit suffers from the disadvantage that it is limited in its inclinable capability and, in addition, it must be used adjacent the table on which the patient is lying and therefore occupies a considerable amount of valuable working space. Such devices are used for diagnostic rather than therapy X-ray treatment. The other known prior art discloses several cassette holding systems which are adjustable but the adjustment is of a vertical or horizontal nature rather than angular. For example see U.S. Pat. Nos. 2,679,442; and 3,555,276.

Another problem encountered in cassette holders lies in the provision of a simple holding mechanism having an adjustment capability. Particular means of holding cassettes are disclosed in U.S. Pat. Nos. 3,771,781 and 3,829,698. These two patents disclose devices having rack and pinion adjustment and a pulley and cable clamping adjustment respectively. These devices are somewhat complicated which results in the disadvantage of relatively expensive construction.

The present cassette holder solves the above and other problems in a manner not disclosed in the known prior art.

SUMMARY OF THE INVENTION

This X-ray cassette holder provides a means of inclining the cassette at a selected angle to suit selected camera positions and of firmly supporting the cassette at said angle so that there is a minimum of discomfort to the patient and maximum utilization of working space.

The holder is particularly useful for therapy X-ray procedures and permits X-ray photographs to be taken of a particular treatment area from several angles without moving the patient. It is readily adaptable for use in conjunction with X-ray machines which have a complete rotation capability so that they can, for example, be directed from a position below the table upwardly through the table at the patient.

This X-ray cassette holder provides a holder plate to which the cassette is attached in adjustable relation. The holder plate is hingedly connected to a base disposed on the X-ray table for swinging movement of the holder plate and the cassette and a support means is provided between the base plate and the holder plate which holds the cassette at a selected angle of inclination without interference in the area forwardly of the cassette between the base plate and the holder plate.

The support means includes an articulated connection provided by a linkage assembly disposed at the rear of the holder plate between the holder plate and the base plate which permits relative swinging movement of the cassette and the selective clamping of the holder plate carrying the cassette at an angle perpendicular to the X-ray camera angle.

The linkage assembly includes a first link hingedly attached to the base plate, a second link hingedly attached to the first link and slidingly connected to the holder plate, and the connection between the second link and the holder plate includes a means of clamping the sliding link to the holder plate.

The sliding link and the holder plate are provided with cooperating calibration marks to indicate the angle of inclination of the cassette.

The holder plate includes a pair of guide arms disposed on either side of the sliding link and adapted to engage the cassette in overlapping relation, said arms being adjustable to suit selective cassette sizes.

In one embodiment the guide arms include an adjustable stop to retain the cassette at a particular elevation.

In another embodiment the base plate is mounted to a table track for lengthwise adjustment relative to the table and said base plate is slotted for transverse movement relative to the table.

This cassette holder is relatively inexpensive to manufacture and is sufficiently simple in operation to be readily understood by an operator with a minimum of training.

BRIEF DESCRIPTION OF THE DRAWINGS

FIG. 1 is a perspective view from the rear of the cassette holder showing the cassette in phantom outline;

FIG. 4 is an exploded view of the cassette holder guide arms;

FIG. 5 is a front view of the sliding link;

FIG. 6 is a perspective view taken from the rear of a modified cassette holder;

FIG. 7 is a detail of the clamping screw holding the sliding link;

FIG. 8 is a detail of the relationship between the track and the base plate clamping screw; and FIG. 9 is a detail of an adjustable guide arm.

DESCRIPTION OF THE PREFERRED EMBODIMENT

Figure 2:
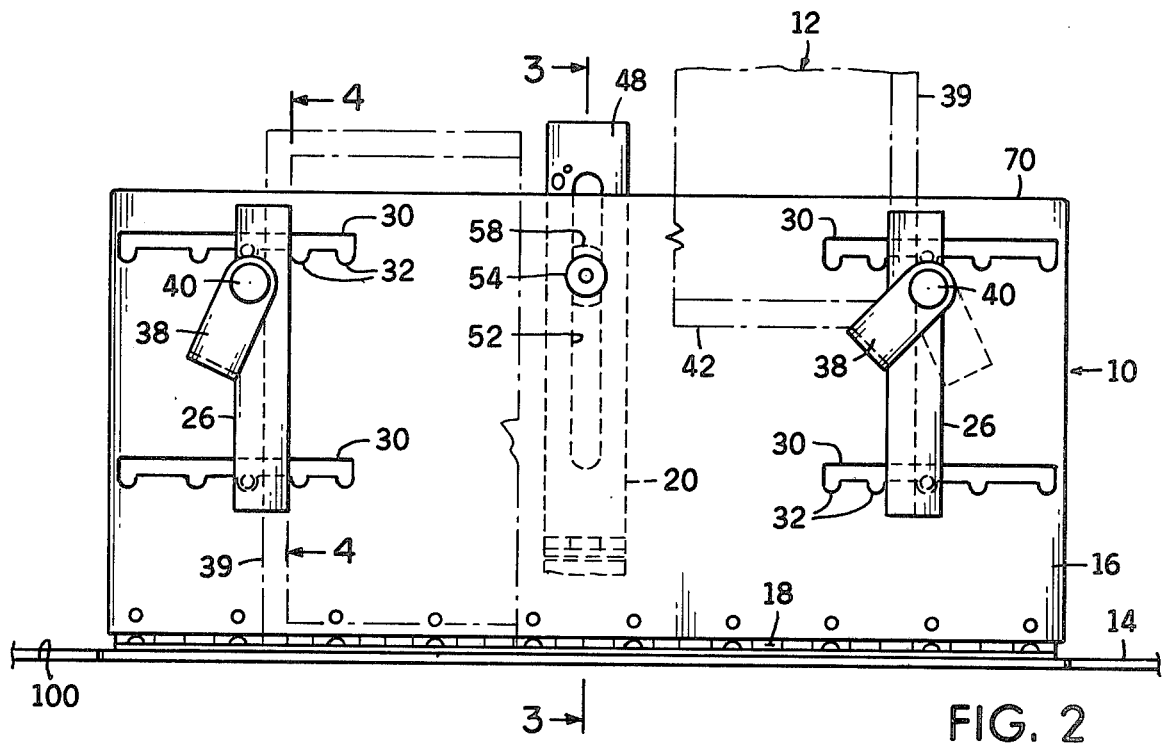
FIG. 2 is a front elevational view of the cassette holder illustrating the cassette in upper and lower positions.

Referring now by reference numerals to the drawings and first to FIG. 1 it will be understood that the cassette holder, generally indicated by numeral 10, is intended for holding an X-ray cassette, shown in phantom outline by numeral 12. The holder 10 includes a base plate 14 to which a holder plate 16 is hingedly attached by means of a piano hinge 18. The holder plate 16 is swingingly related to said base plate and is supported at a desired angle of elevation by a support means generally indicated by numeral 20. The component parts of the device will now be more specifically described.

Figure 3:
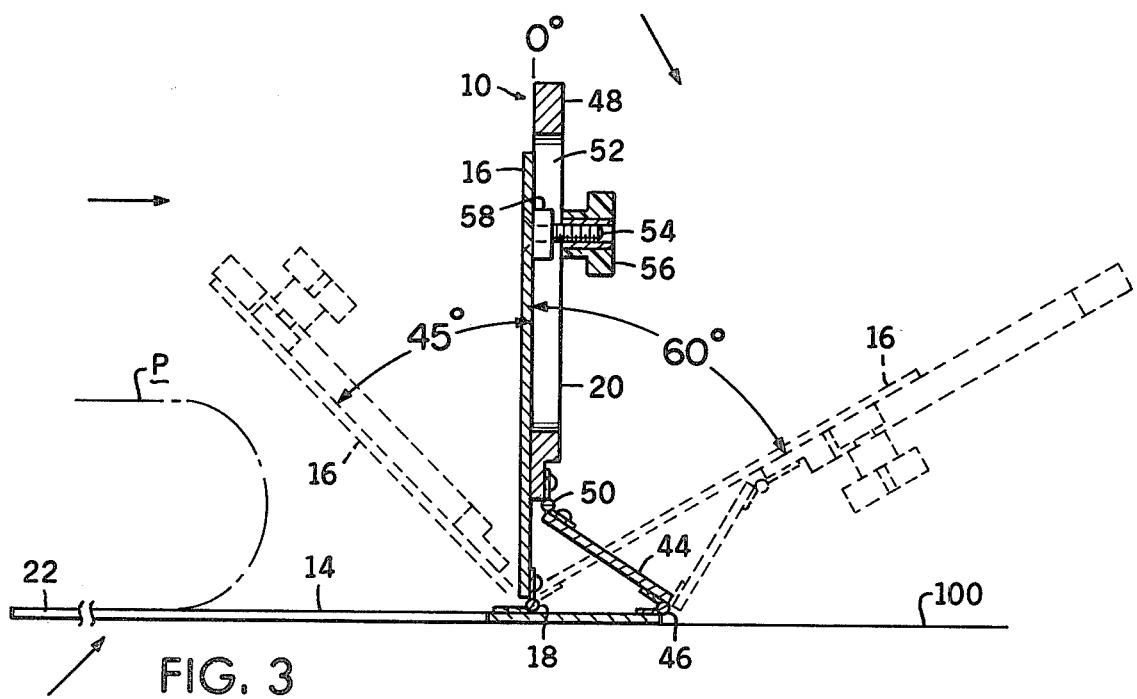
FIG. 3 is a cross sectional view taken on line 3—3 of FIG. 2 illustrating the holder in vertical, forwardly inclined and rearwardly inclined dispositions.

The base plate 14 is substantially U-shaped and includes a pair of arms 22 and a bight portion 24. It is intended that the base plate 14 be disposed upon a flat examination table 100 below the patient to be examined as shown in FIG. 3 in which, for example, the shoulder of the patient is indicated in phantom outline by P. The holder plate 16 is generally rectangular in configuration and is provided with a pair of laterally adjustable, opposed guide arms 26. The guide arms 26, as shown in FIG. 4 are provided with fixed threaded elements 28 which extend through slots 30 provided in the holder plate 16, said slots having a plurality of detent portions 32 receiving said threaded elements and providing predetermined positioning points for the guide arms 26. The threaded elements 28 are provided with clamping nuts 34 to hold the guide arms 26 in position and said guide arms include elongate lips 36 which overlap the cassette sides 39 and retain the cassette 12 in position. As shown in FIGS. 2 and 4 the guide arms 26 also include a pivoted L-shaped stop element 38 held in place by a pivot screw 40. As shown on the right hand side of FIG. 2, these elements have the capability of being pivoted from an inoperative position, shown in broken lines on the outside of the guide arms 26, about the upper portion of said guide arms to an operative position on the inside of said guide arms. It will be understood that in the operative position, when both elements 38 are inside the guide arms, they engage the cassette lower edge 42 and hold the cassette 12 in a predetermined position.

The support assembly 20 by which the holder plate 16 is held in inclined relation to the base plate 14 is essentially an articulated linkage system which is best understood by reference to FIGS. 1 and 3. The system includes a short link 44 hingedly attached to the base plate bight portion 24 by means of a hinge element 46, and a sliding link 48 which is hingedly attached to the short link 44 by means of a hinge element 50. The sliding link 48 includes a slot 52, which receives a threaded element 54. The threaded element 54 is fixedly attached to the holder plate 16 and a clamping nut 56 provides a connecting means by which the sliding link 48 is selectively clamped to the holder plate 16, and thereby provides a means for holding said first and second link means together at a selected angular relation to each other. A spacer element 58 is provided (see FIG. 7) to insure accurate alignment of the sliding link 48 relative to the holder plate 16.

As clearly shown in FIGS. 1, 2 and 5 a double calibration system is provided to permit the observer to ascertain the forward and rearward angle of inclination of the holder plate 16, and therefore of the X-ray cassette 12. As shown in FIG. 1, the forward inclination is indicated by a plurality of angle of inclination calibration marks eg 0, 10, 20, 30, 40 and 45 degrees, provided on the holder plate 16, which are shown collectively by numeral 60. The marks are read against a marker 62 on sliding link 48 for determining the forward angle of inclination of the cassette 12. As shown in FIGS. 2 and 5 the rearward angle of inclination is indicated by means of a plurality of calibration marks eg 0, 10, 20, 30, 40, 50 and 60 degrees provided on the sliding link inside face 68, which are shown collectively by numeral 66 in FIG. 5. As shown in FIG. 2 the marks are read against a marker provided by the upper edge 70 of the holder plate 16. Thus, when the holder plate 16 is inclined forwardly as shown in FIG. 3 the angle of inclination is read by means of calibration marks 60, and when said holder plate is disposed rearwardly the angle of inclination is read by means of the calibration marks 66.

It is thought that the structural features and functional advantages of this X-ray cassette holder have become fully apparent from the foregoing description of parts but for completeness of disclosure the use of the device will be briefly described with reference to FIGS. 1, 2, 3 and 5.

Initially, the holder plate guide arms 26 are laterally adjusted to a position to suit the width of the particular cassette 12 to be used and clamped in that position. The base plate arms 22 are then slipped under the patient P on the table 100, see FIG. 3, and the cassette 12 is inserted between said guide arms. If a vertical position is desired, to suit a camera direction indicated by the horizontal arrow in FIG. 3, the holder plate 16 is rotated until the marker 64 on the sliding link 48 is aligned with the 0° calibration mark on the holder plate 16 and clamped in position. Alternatively, as shown in FIGS. 2 and 5 the holder plate upper edge 70 can be aligned with the 0° calibration mark on the sliding link inside face 68. If an angular variation from the vertical is desired, for example a forward inclination of 45°, to suit a camera direction indicated by the upwardly inclined arrow in FIG. 3, the marker 64 on the sliding link 48 is aligned with the 45° calibration mark on the holder plate 16 and clamped in position. If a rearward inclination, for example 60° is desired to suit a camera direction indicated by the downwardly inclined arrow in FIG. 3, the marker edge 70 is aligned with the 60° calibration mark on the sliding link inside face and clamped in position.

The cassette 12 is supported at the lower end by the table 100. However, by the use of the L-shaped stop elements 38, the cassette 12 can be retained in an elevated position away from the table 100. It will be understood that, if desired, the arms 26 can be made narrower so that the overlap effectively clamps the cassette 12 in a selected elevated position relative to the holder plate 16 when nuts 34 are tightened.

Referring now to the modified device represented by FIGS. 6 through 9 it will be understood that the holder 110 is used for holding a cassette 112. The holder 110 includes a base plate 114 to which a holder plate 116 is hingedly attached as by a piano hinge 118. The holder plate 116 is supported by a support assembly 120 which is substantially identical to the support assembly 20 described above. For purposes of simplicity the calibration system, which is also identical to that discussed above, has been omitted.

The modified device 110 shown in FIG. 6 is intended primarily for diagnostic use and differs from that of the first embodiment already described with respect to the construction of the base plate 114 and the holder plate 116. The base plate 114 is adapted for use with a diagnostic table 200 of the type provided with a track 202 attached to said table, said table and base plate providing, in effect, fixed and movable portions of a base means. The track 202 includes a channel-shaped portion 204 defining a groove receiving a pair of sliding bolts 206 therewithin said bolts being shown in FIG. 8 and including a clamping nut 208. As clearly shown in FIG. 6 the base plate 114 includes a pair of parallel slots 122 which receive the bolt elements 206 in sliding relation and provide a means by which the holder 110 can be moved transversely relative to the longitudinal trace 202, said movement being measured by calibration marks disposed on the base plate 114 and collectively indicated by numeral 124. The holder plate 116 is provided with a pair of guide arms 126 having threaded elements 128 attached thereto and being received within slots 130 provided in the holder plate 116. The guide arms 126 are formed to include a lug portion 132 at the base of the threaded element 128 which precludes rotation of said guide arms relative to said holder plate and insures accurate alignment with the cassettes 112. Lips 136 provided on the side arms 126 overlappingly engage the sides 138 of said cassette in sliding relation. The guide arms are clamped in position by means of threaded clamping nut 134 which threadedly engages the element 128.

The support assembly 120 is substantially identical to that discussed above with respect to the first embodiment and includes a short link 144 hinged to the base plate 114 by means of a hinge element 146, and a sliding link 148 attached to said short link by means of a hinge element 150. The sliding link includes a slot 152 receiving a threaded element 154 (FIG. 7) attached to the holder plate 116, and a clamping nut 156 is threadedly received by said element to hold said sliding link 148 in position, a spacer 158 being mounted on said element and being received in sliding relation within said slot 152.

The holder 110 is used in substantially the same manner as described above with respect to the first embodiment insofar as the holder plate inclination is concerned, although, as will be understood, the guide arms 136 have a wider range of lateral adjustment capability. The longitudinal and transverse positioning capability of the holder 110 is different from that for the first embodiment because the device is intended for use with a tracked table. In effect, the device as a whole can be readily moved longitudinally of the table without affecting the disposition of the patient because of the rearwardly directed base plate 114. Further, the provision of slots in said base plate together with the cooperating clamp means provided by the sliding bolts permits transverse movement of the holder 110 and even some horizontal, rotational movement of said holder, in the manner of a turn table, should this be desired.

We claim as our invention:

1. A holder for an x-ray cassette, comprising:
   (a) base means,
   (b) holder means for the cassette,
   (c) hinge means connecting the holder means to the base means for swinging movement of said holder means relative to said base means,
   (d) support means between the base means and the holder means supporting the holder means relative to the base means at a selected angle of inclination, said support means including:
      (1) a first link means hingedly attached to one of said base means and holder means,
      (2) a second relatively elongate link means hingedly attached to the first link means and slidingly related to said one of said base means and holder means in a direction lengthwise of said second link means, and
      (3) clamping means selectively clamping the sliding second link means to the other of said base means and holder means in adjustable relation, and
   (e) said holder means including a plate,
   (f) the second link means extending generally perpendicularly of the axis of swinging movement in substantially parallel sliding relation with said plate, and
   (g) said holder means including a pair of spaced guide arm substantially parallel to said second link means and attached to said plate on either side of said support means and adapted to engage said cassette in overlapping retaining relation.

2. A holder as defined in claim 1, in which:
   (h) said arms are adjustably related to said plate on each side of said elongate link to selectively receive cassettes of different widths.

3. A holder as defined in claim 1, in which:
   (h) said arms include stop means pivoted thereto and selectively movable from a cassette engageable position to a non-engageable position to determine the lengthwise retention disposition of said cassette relative to said holder plate.

4. A holder for an X-ray cassette, comprising:
   (a) base means,
   (b) holder means for the cassette,
   (c) hinge means connecting the holder means to the base means for swinging movement of said holder means relative to said base means,
   (d) support means between the base means and the holder means supporting the holder means relative to the base means at a selected angle of inclination, said support means including:
      (1) a first link means hingedly attached to one of said base means and holder means,
      (2) a second link means hingedly attached to the first link means, and
      (3) connecting means selectively connecting the second link means to the other of said base means and holder means
   (e) said base means including a fixed portion and a movable portion mounted to said fixed portion in sliding relation, and
   (f) said holder means including a plate portion hingedly attached to said movable portion.

5. A holder as defined in claim 4, in which:
   (g) the fixed portion of said base means includes a track means and said movable portion includes a plate portion adapted for longitudinal movement relative to said track means and transverse movement relative to said track means.

6. A holder as defined in claim 5, in which:
   (h) said base means plate portion includes a pair of slots disposed in transverse relation to said track means and a pair of clamping elements engageable within said slots and said track means to selectively fix the location of said plate portion longitudinally and transversely relative to said fixed portion.

* * * * *